United States Patent
Rodriguez et al.

(10) Patent No.: US 7,610,089 B1
(45) Date of Patent: Oct. 27, 2009

(54) IMPLANTABLE STRAIN SENSOR FOR MEDICAL DIAGNOSTICS

(75) Inventors: Rodolfo Rodriguez, Santa Monica, CA (US); Annapurna Karicherla, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 321 days.

(21) Appl. No.: 11/677,536

(22) Filed: Feb. 21, 2007

(51) Int. Cl.
*A61N 1/365* (2006.01)

(52) U.S. Cl. .................. 607/19; 310/317; 310/338; 310/331; 73/504.04

(58) Field of Classification Search ............ 607/9, 607/12, 14, 17, 18, 19
See application file for complete search history.

(56) References Cited

U.S. PATENT DOCUMENTS

| | | | |
|---|---|---|---|
| 4,089,927 A * | 5/1978 | Taylor | 310/331 |
| 4,998,975 A | 3/1991 | Cohen et al. | |
| 5,496,352 A * | 3/1996 | Renger | 607/19 |
| 5,716,382 A | 2/1998 | Snell | |
| 5,974,341 A | 10/1999 | Er et al. | |
| 5,987,985 A * | 11/1999 | Okada | 73/504.04 |
| 6,252,335 B1 | 6/2001 | Nilsson et al. | |
| 6,529,777 B1 | 3/2003 | Hornstrom et al. | |
| 7,021,141 B1 | 4/2006 | Nilsson et al. | |
| 2005/0200236 A1* | 9/2005 | Buhler et al. | 310/317 |
| 2005/0200243 A1* | 9/2005 | Spangler et al. | 310/338 |

FOREIGN PATENT DOCUMENTS

WO  2006050385 A2  5/2006

* cited by examiner

*Primary Examiner*—Carl H Layno
*Assistant Examiner*—Elizabeth K So

(57) ABSTRACT

Embodiments include strain sensor devices for detecting movement, morphological changes or other physical parameters within a patient's body tissue. Some embodiments are directed specifically to measuring parameters within a patient's heart and may also be configured to communicate with an implantable stimulation device and associated external programming device.

27 Claims, 10 Drawing Sheets

IMPLANTABLE STRAIN SENSOR FOR MEDICAL DIAGNOSTICS

FIELD OF THE INVENTION

Embodiments of the present invention generally relate to implantable medical devices such as implantable electrical stimulation devices including pacemakers, implantable cardioverter/defibrillators (ICDs) and the like. In particular, embodiments of the invention are directed to strain sensors and methods of using same that may be used to communicate clinical information to stimulation devices such as pacemakers, ICDs and the like to treat patients. Embodiments of the strain sensors may also be used to communicate clinical information to external programmer devices, either directly or indirectly, used in association with such stimulation devices.

BACKGROUND

Pacing of a patient's heart is a useful treatment modality for many different conditions. Some pacing or tissue stimulation treatment methods require or benefit from feedback of clinical information from the patient's heart in order to be properly timed or synchronized. Some of this feedback may be obtained by the sensing of electrical signals from cardiac tissue or the like, however, electrical signals or information often do not accurately indicate the physical state or position of the patient's heart or portions thereof. Strain sensors that measure physical movement of tissue may be useful in many situations to provide information of the physical state or position or movement of cardiac tissue. In particular, piezoelectric strain sensors may be useful for such indications. However, known piezoelectric strain sensors do not necessarily account for the type of cyclic loading and sensitivity needed for cardiac applications. What has been needed are piezoelectric strain sensors that have a high sensitivity and provide a high signal to noise output. What has also been needed are piezoelectric strain sensors that can accommodate the cyclic loading associated with cardiac tissue and other body tissues that undergo significant cyclic loading.

SUMMARY

Some embodiments of a piezoelectric strain sensor for use within a patient's body include a first resilient shear layer, a second resilient shear layer disposed apart from and substantially parallel to the first resilient shear layer and a piezoelectric element disposed between and secured to the first resilient shear layer and second resilient shear layer. The piezoelectric element is secured to the first and second resilient shear layers such that the first resilient shear layer and second resilient shear layer are configured to apply shear strain onto the piezoelectric element upon bending of the first resilient shear layer and second resilient shear layer. A compliant filler material is disposed between the first resilient shear layer and second resilient shear layer. Some embodiments include an implantable piezoelectric strain sensor having a hermetic seal coating with a dielectric layer and a thin noble metal layer disposed outside of the dielectric layer.

Some embodiments of a piezoelectric strain sensor for use within a patient's body include a first resilient shear layer and a second resilient shear layer disposed apart from and substantially parallel to the first resilient shear layer. A first piezoelectric element is disposed transversely away from a longitudinal center line of the first resilient shear layer and a longitudinal center line of the second resilient shear layer and has a first side secured to the first resilient shear layer, a second side opposite the first side and secured to the second resilient shear layer. The first piezoelectric element also has a thickness dimension between the first side and second side, a major transverse dimension that is substantially greater than the thickness dimension and a polarization direction extending from the second side to the first side of the piezoelectric element in an orientation that is substantially perpendicular to the second side of the piezoelectric element. A second piezoelectric element is disposed opposite the longitudinal center line of the first piezoelectric element and has a first side secured to the first resilient shear layer and a second side opposite the first side which is secured to the second resilient shear layer. The second piezoelectric element also has a thickness dimension between the first side and second side, a major transverse dimension that is substantially greater than the thickness dimension and a polarization direction extending from the first side to the second side of the piezoelectric element in an orientation that is substantially perpendicular to the first side of the piezoelectric element. A compliant filler material is disposed between the first resilient shear layer and second resilient shear layer around the first and second piezoelectric elements.

Some embodiments of this piezoelectric strain sensor also include a third resilient shear layer disposed apart from and substantially parallel to the second resilient shear layer. A third piezoelectric element is disposed transversely away from the longitudinal center line of the second resilient shear layer and a longitudinal center line of the third resilient shear layer. The third piezoelectric element has a first side secured to the second resilient shear layer and a second side opposite the first side secured to the third resilient shear layer. The third piezoelectric element also has a thickness dimension between the first side and second side, a major transverse dimension that is substantially greater than the thickness dimension and a polarization direction extending from the second side to the first side of the piezoelectric element in an orientation that is substantially perpendicular to the second side of the piezoelectric element. A fourth piezoelectric element is disposed opposite the longitudinal center line of the second resilient shear layer from the third piezoelectric element and has a first side secured to the second resilient shear layer and a second side opposite the first side secured to the third resilient shear layer. The fourth piezoelectric element also has a thickness dimension between the first side and second side, a major transverse dimension that is substantially greater than the thickness dimension and a polarization direction extending from the first side to the second side of the piezoelectric element in an orientation that is substantially perpendicular to the first side of the piezoelectric element. A compliant filler material is disposed between the second resilient shear layer and third resilient shear layer around the third and fourth piezoelectric elements.

Some embodiments of a tissue stimulation system include an implantable stimulation device and a strain sensor in communication with the implantable stimulation device. The strain sensor includes a first resilient shear layer, a second resilient shear layer disposed apart from and substantially parallel to the first resilient shear layer and a piezoelectric element disposed between and secured to the first resilient shear layer and second resilient shear layer with the first resilient shear layer and second resilient shear layer configured to apply shear strain onto the piezoelectric element upon bending of the first resilient shear layer and second resilient shear layer. A compliant filler material is also disposed between the first resilient shear layer and second resilient shear layer.

These features of embodiments will become more apparent from the following detailed description when taken in conjunction with the accompanying exemplary drawings.

BRIEF DESCRIPTION OF THE DRAWINGS

FIG. 3 is a block diagram of portions of an embodiment of an external programmer for use in processing and displaying event codes, counters, IEGM signals and the like.

DETAILED DESCRIPTION

Embodiments discussed herein relate to cardiac pacing methods, cardiac sensing methods and associated devices designed to relieve a variety of conditions that result from cardiac disease as well as other conditions. In order to pace or otherwise impart electrically delivered therapy to a patient's tissue, such as heart tissue, an electrical lead or delivery system is typically required. An electrical lead is used to deliver a therapeutic signal from a stimulation device to a target tissue site of the patient's body. Following is a general discussion of stimulation device embodiments that may be used with electric lead and stimulation method embodiments discussed herein.

Overview of Stimulation Device Embodiments

Figure 1:
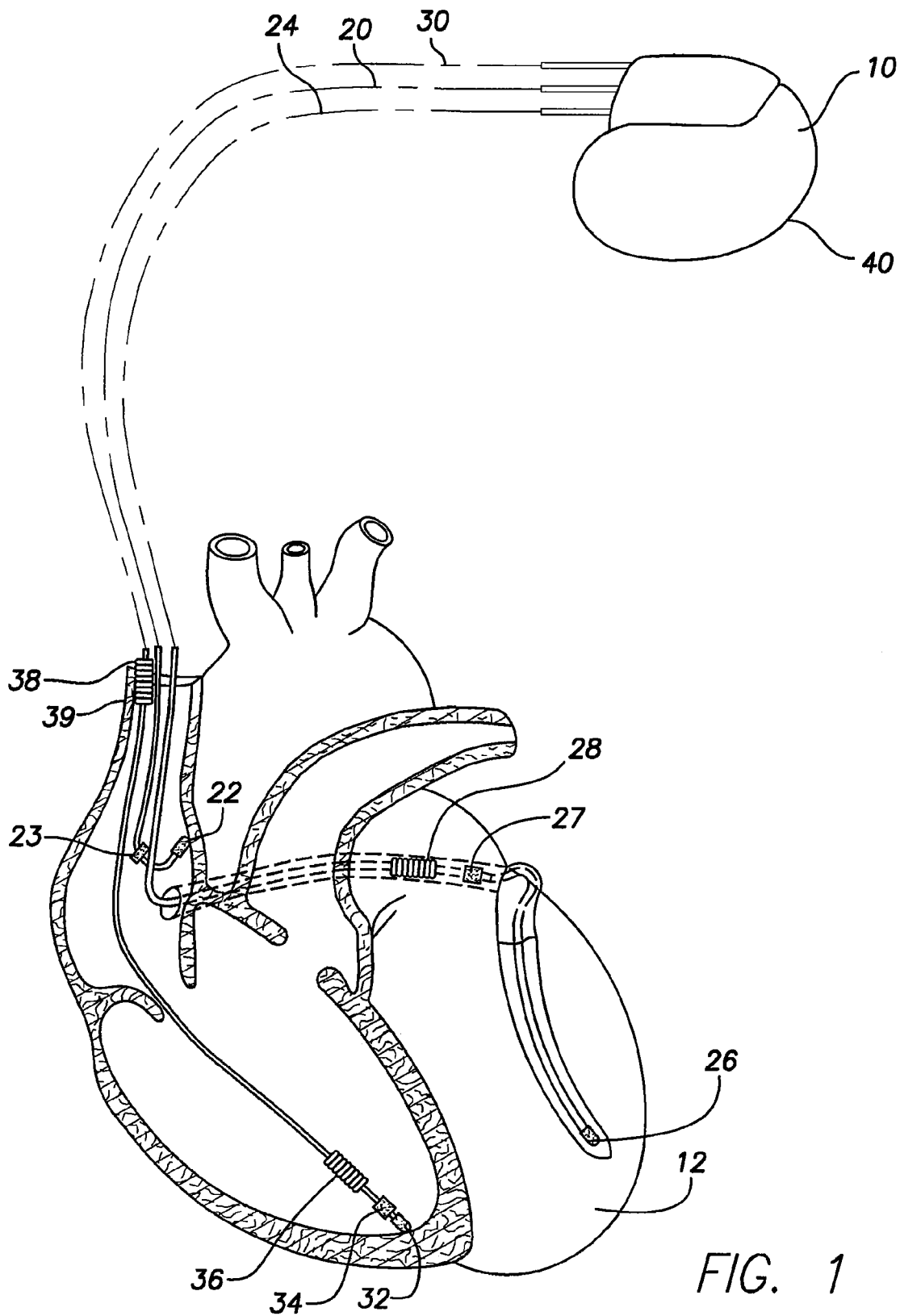
FIG. 1 is a simplified diagram illustrating an implantable cardiac stimulation device in electrical communication with at least three electrical leads implanted in or on the heart of a patient.

FIG. 1 shows a stimulation device 10 in electrical communication with the heart 12 of a patient with three electrical leads, 20, 24 and 30, in a configuration suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava 39. Accordingly, the right ventricular lead 30 is capable of receiving cardiac signals, and delivering stimulation in the form of pacing and shock therapy to the right ventricle. The stimulation device 10 includes an outer housing 40 that may be electrically conductive.

Figure 2:
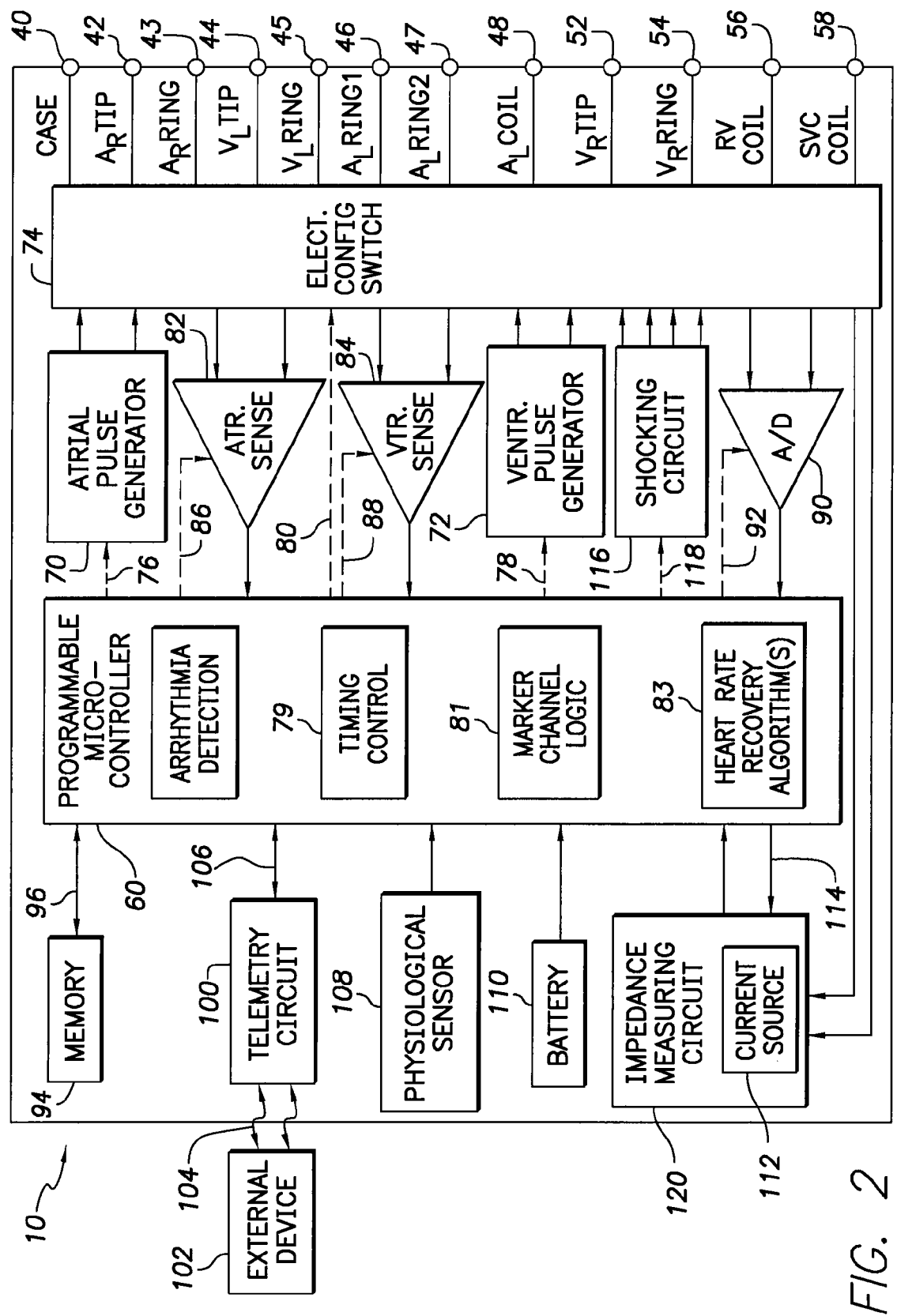
FIG. 2 is a functional block diagram of a multi-chamber implantable stimulation device illustrating exemplary basic elements of a stimulation device which can provide cardioversion, defibrillation, and/or pacing stimulation in up to four chambers of the heart.

As illustrated in FIG. 2, a simplified block diagram is shown of the multi-chamber implantable cardiac stimulation device 10, which is capable of treating both fast and slow arrhythmias with stimulation therapy, including cardioversion, defibrillation, and pacing stimulation. While a particular multi-chamber device is shown, this is for illustration purposes only, and appropriate circuitry may be duplicated, eliminated or disabled in any desired combination to provide a device capable of treating the appropriate chamber(s) with cardioversion, defibrillation and pacing stimulation. In addition, some processing step embodiments discussed below may be implemented in the form of software instructions that are resident on a computer-readable media that is included with the stimulation device 10.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 45, 46, 47, 48, 52, 54, 56 and 58 (shown schematically and, for convenience, the names of the electrodes to which they are connected are shown next to the terminals). While it is recognized that the number of terminals of current devices may be limited due to international standards, some terminals/electrodes may be programmably eliminated/selected in order to accommodate various embodiments. In addition, standards may change in the future and accommodate additional configurations.

To achieve right atrial sensing and pacing, the connector includes at least a right atrial tip terminal ($A_R$ TIP) 42 and a right atrial ring terminal ($A_R$ RING) 43, adapted for connection to the atrial tip electrode 22 and atrial ring electrode 23, respectively. To achieve left chamber sensing, pacing and shocking, the connector includes a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a controller in the form of a programmable microcontroller 60, which controls the various modes of stimulation therapy. The microcontroller 60 (also referred to herein as a controller or control unit) includes a microprocessor, or equivalent control circuitry, designed specifically for detecting sensed cardiac function data, generating warning signals that may be felt, heard or seen by a patient, controlling delivery of stimulation therapy as well as other function and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein. Microprocessor-based control circuits for performing timing and data analysis functions may be used.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. In order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 also includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, blanking intervals, noise detection windows, evoked response windows, alert intervals, marker channel timing (via marker channel logic 81), etc. Some embodiments of the microcontroller 60 are programmed with one or more heart rate recovery algorithms 83. The heart rate recovery algorithm(s) operate to monitor a patient's heart rate recovery when, for example, the patient recovers from a period of exercise to a period of rest. The algorithms can then save data associated with the heart rate recovery.

Switch bank 74 includes a plurality of switches for connecting the desired electrodes to the appropriate I/O circuits, thereby providing complete electrode programmability. The switch 74, in response to a control signal 80 from the microcontroller 60, determines the polarity of the stimulation pulses (e.g., unipolar, bipolar, combipolar, etc.) and various shocking vectors by selectively closing the appropriate combination of switches (not shown). Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. The atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches. In this way, the clinician may program the sensing polarity independent of the stimulation polarity.

Each sensing circuit, 82 and 84, preferably employs one or more low power, precision amplifiers with programmable gain and/or automatic gain control, band pass filtering, and a threshold detection circuit to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the stimulation device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia or other clinical condition. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy"). The atrial and ventricular sensing circuits 82 and 84 receive control signals over signal lines 86 and 88 from the microcontroller 60, for controlling gain, threshold, polarization charge removal circuitry, and the timing of any blocking circuitry coupled to the inputs of the atrial and ventricular sensing circuits 82 and 84.

Cardiac signals may also be applied to the inputs of an analog-to-digital (A/D) data acquisition system 90. The data acquisition system 90 may be configured to acquire intracardiac electrogram signals, convert the raw analog data into a digital signal, and store the digital signals for later processing and/or telemetric transmission to an external device 102. The microcontroller 60 enables the data acquisition system 90 via control signal 92 to sample the cardiac signal that falls within a capture detection window. The data acquisition system 90 is coupled to the right atrial lead 20, the coronary sinus lead 24, and the right ventricular lead 30 through the switch 74 to sample cardiac signals across any pair of desired electrodes. The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, wave shape and vector of each shocking pulse to be delivered to the patient's heart 12 within each respective tier of therapy.

The operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 allows intracardiac electrograms and status information relating to the operation of the device 10 (as contained in the microcontroller 60 or memory 94) to be sent to the external device 102 through an established communication link 104.

In some embodiments, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). A physiological parameter of the heart, which may be measured to optimize such pacing and to indicate when such pacing may be inhibited or terminated is the stroke volume of the heart. Accordingly, the microcontroller 60 responds by adjusting the various pacing parameters (such as rate, AV Delay, V-V Delay, etc.) at which the atrial and ventricular pulse generators, 70 and 72, generate stimulation pulses. A common type of rate responsive sensor is an activity sensor, such as an accelerometer or a piezoelectric crystal, which is mounted within the housing 40 of the stimulation device 10. While shown as being included within the stimulation device 10, the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may use lithium/silver vanadium oxide batteries.

In the case where the stimulation device 10 is intended to operate as an implantable cardioverter/defibrillator (ICD) device, it detects the occurrence of an arrhythmia and automatically applies an appropriate electrical shock therapy to the heart aimed at terminating the detected arrhythmia. The microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left atrial coil electrode 28, the RV coil electrode 36, and/or the SVC coil electrode 38, as shown in FIG. 1. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As further shown in FIG. 2, the device 10 is shown as having an impedance measuring circuit 120 including an impedance measuring current source 112 and a voltage measuring circuit 90 (shown in FIG. 2 as an A/D converter), which may be enabled by the microcontroller 60 via a control signal 114 for providing stroke volume measurements of the heart 12. The current source 112 can provide an alternating or pulsed excitation current. The voltage measuring circuitry 90 may also take the form of, for example, a differential amplifier. The uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring a respiration parameter (for example, tidal volume, respiration rate, minute ventilation or volume, abnormal or periodic breathing); measuring thoracic impedance for determining shock thresholds and shock timing (corresponding to the diastolic time); detecting when the device has been implanted; measuring a cardiac parameter (such as, stroke volume, wall thickness, left ventricular volume, etc.); and detecting the opening of the valves etc.

External Programmer

Figure 3:
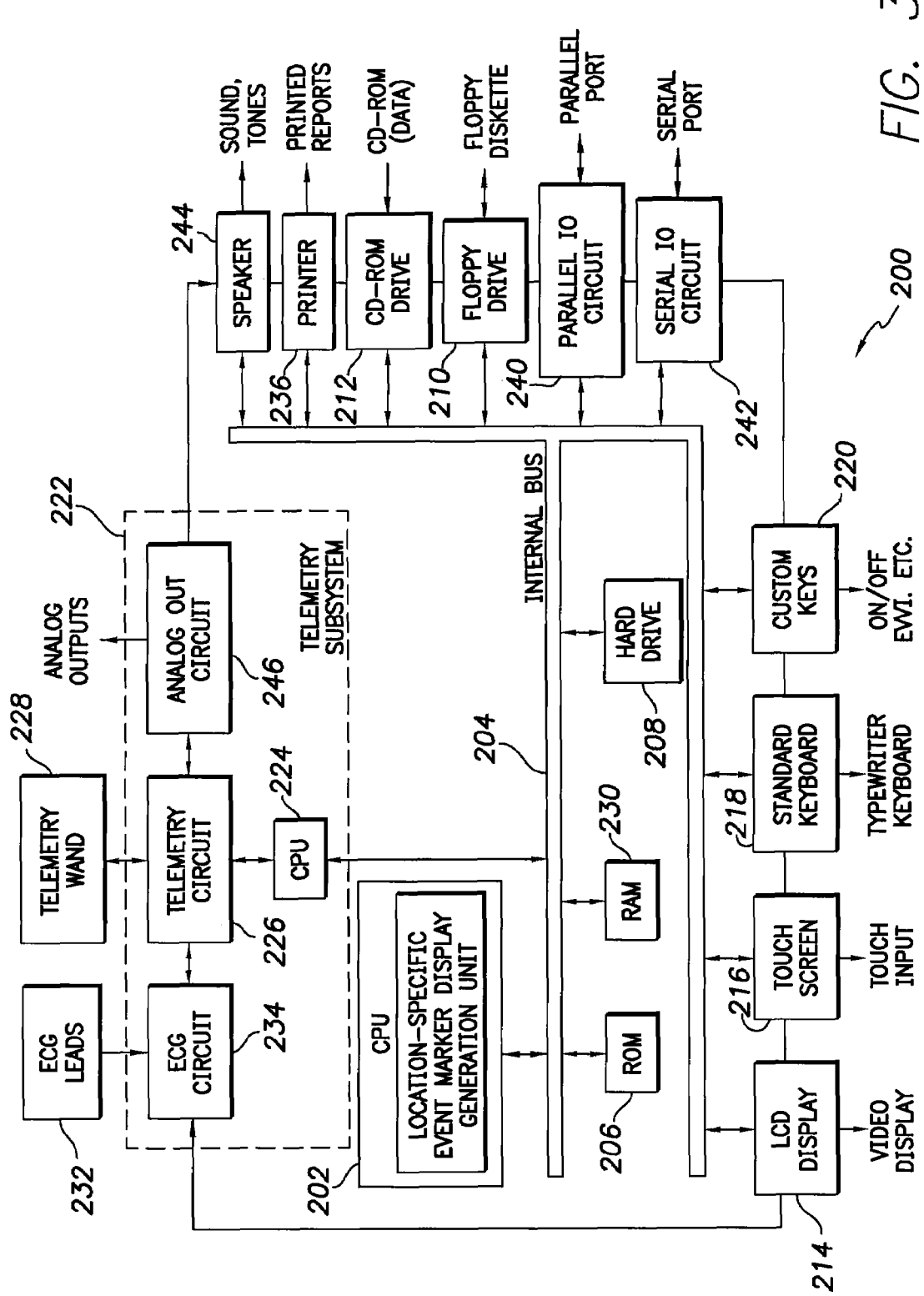
Figure 4:
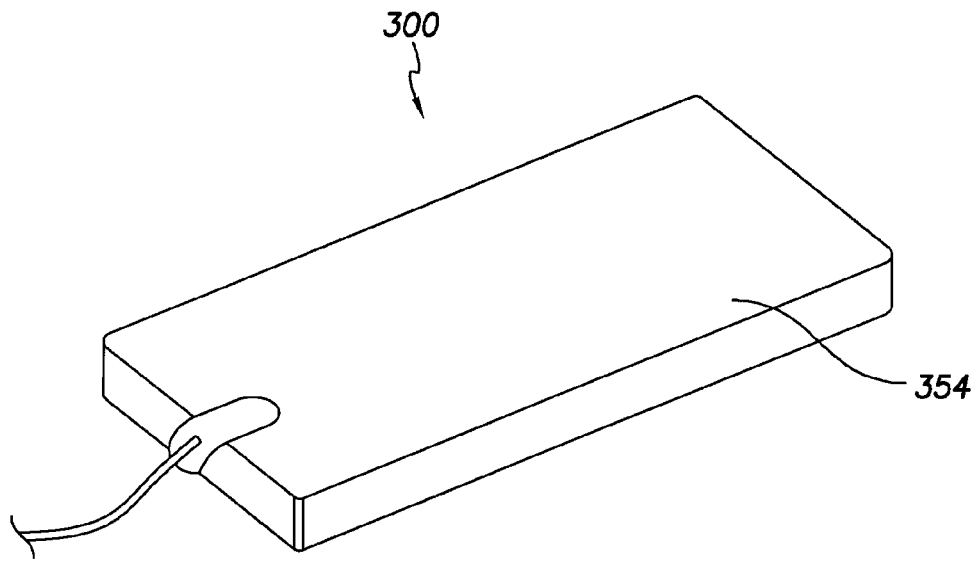
FIG. 4 is a perspective view of an embodiment of a strain sensor.
Figure 5:
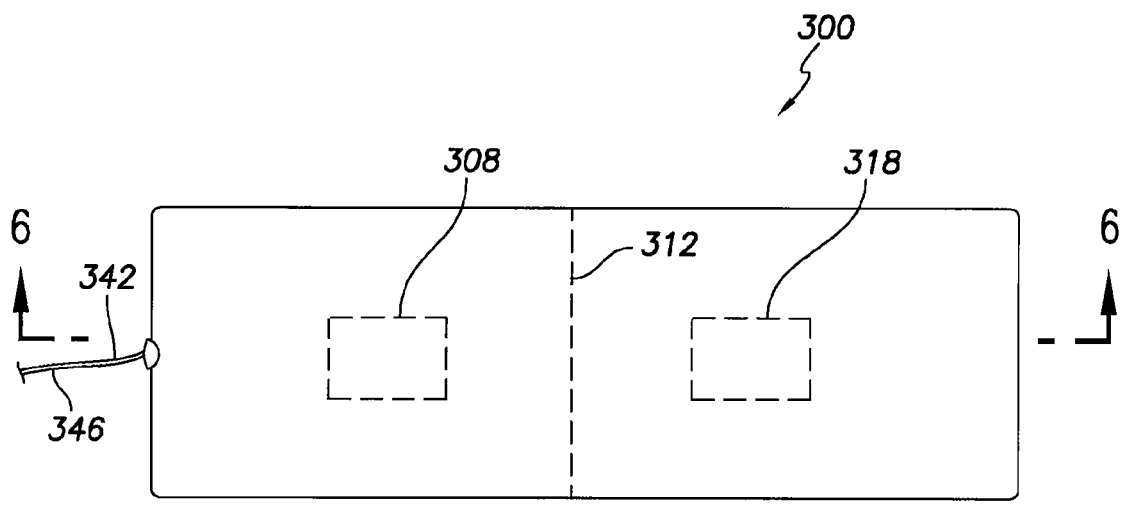
FIG. 5 is a top view of the strain sensor of FIG. 4.
Figure 6:
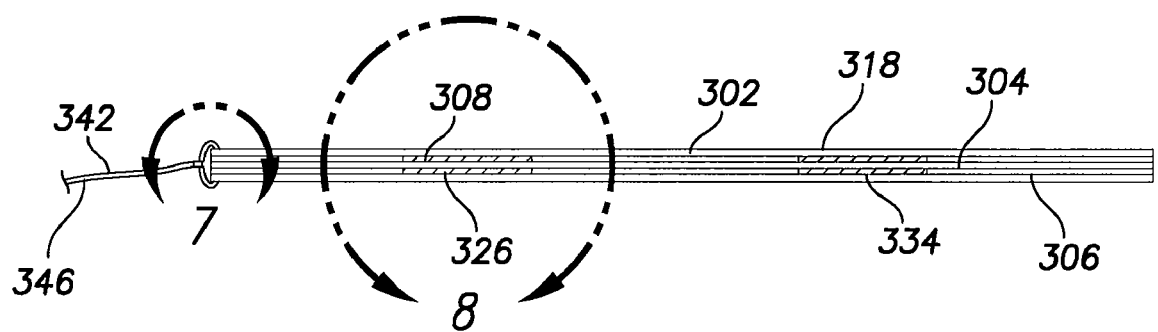
FIG. 6 is a view of the strain sensor of FIG. 5 in longitudinal section taken along lines 6-6 of FIG. 5.

FIG. 3 illustrates pertinent components of an external programmer 200 for use in programming an implantable cardiac stimulation device such as the stimulation device 10 of FIGS. 2 and 3. Such programmer embodiments permit a physician or other user to program the operation of the implanted stimulation device 10 and to retrieve and display information received from the implanted device 10 such as IEGM data and device diagnostic data. In particular, the programmer 200 is provided with internal components capable of separately receiving, storing and processing event markers representative of events paced or sensed in any of the four chambers of the heart. Additionally, the external programmer 200 receives and displays ECG data from separate external ECG leads that may be attached to the patient. Depending upon the specific programming of the external programmer, programmer 200 may also be capable of processing and analyzing data received from the implanted device and from the ECG leads to, for example, render preliminary diagnosis as to medical conditions of the patient or to the operations of the implanted device.

Operations of the programmer 200 are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206. Additional software may be accessed from a hard drive 208, floppy drive 210, and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an EWI key.

Typically, the physician initially controls the programmer 200 to retrieve data stored within the implanted cardiac stimulation device and to also retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via the internal bus. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient in the vicinity of the implanted device to permit reliable transmission of data between the telemetry wand and the implanted device.

Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Preferably, all data stored within the implanted device is recorded within "event records" which facilitate the efficient storage and transmission of the data. The data provided by the stimulation device 10 and the event markers displayed by the external programmer 200 distinguish among a greater number of sensing locations, such as between the left and right chambers of the heart or among multiple locations within a single chamber of the heart.

For some embodiments, the memory of the external programmer 200 stores the location-specific event records, counter data and IEGM data for each of the four chambers of the heart received from the stimulation device 10. ROM 206 stores location-specific event records, counter data and IEGM data for each of the four chambers of the heart. A location-specific event marker display generation unit within the CPU controls the generation of graphic displays of diagnostic information based on the location-specific event records, counter data and IEGM data stored in ROM 206. The location-specific event processing unit may be a software module of a control program executed by the CPU 202.

Data retrieved from the implanted stimulation device 10 is stored by external programmer 200 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 200, the implanted device 10 may be further controlled to transmit additional data in real time as it is detected by the implanted device 10, such as additional IEGM data, lead impedance data, and the like. Additionally, or in the alternative, telemetry subsystem 222 receives ECG signals from ECG leads 232 via an ECG processing circuit 234. As with data retrieved from the implanted stimulation device 10 itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time.

Thus the programmer 200 receives data both from the implanted device 10 and from the external ECG leads. Data retrieved from the implanted device 10 includes parameters representative of the current programming state of the implanted device. Under the control of the physician, the external programmer 200 displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Techniques for programming an implanted cardiac stimulation device may be found in U.S. Pat. No. 5,716,382 entitled "Programmer for an Implantable Cardiac Stimulating Device" filed Aug. 2, 1995, by S. Snell, which is incorporated by reference herein in its entirety. Prior to reprogramming specific parameters, the physician may control the external programmer to display any or all of the data retrieved from the implanted device or from the ECG leads, including displays of ECGs, IEGMs, and statistical patient information. In particular, the external programmer can be controlled to generate graphic displays or printouts of location-specific; IEGMs and event markers.

Depending upon the programming of the external programmer and the commands entered, the programmer may display either a single combined IEGM representative of a combination of the IEGM signals from the four chambers of the heart or may display the individual IEGM signals separately. Further information pertaining to information that may be displayed using the programmer may be found in U.S. Pat. No. 5,974,341 entitled "Method and Apparatus for Detecting and Displaying Diagnostic Information in Conjunction with Intracardiac Electrograms and Surface Electrocardiograms" filed Dec. 22, 1997, by S. Er et al. which is incorporated by reference herein in its entirety. Any or all of the information displayed by programmer 200 may also be printed using a printer 236.

Programmer 200 also includes a modem to permit direct transmission of data to other programmers via the public switched telephone network (PSTN) or other interconnection line, such as a T1 line or fiber optic cable. Depending upon the implementation, the modem may be connected directly to internal bus 204 or may be connected to the internal bus 204 via either a serial port 242 or a parallel port 240. Other peripheral devices may be connected to the external programmer via serial port 242 or a parallel port 240 as well. Although one of each is shown, a plurality of input output (IO) ports may be provided. A speaker 244 is included for providing audible tones to the user, such as a warning beep in the event the physician provides improper input. Telemetry subsystem 222 additionally includes an analog output circuit 246 for controlling the transmission of analog output signals.

With the programmer 200 configured as shown, a physician or other user operating the external programmer is capable of retrieving, processing and displaying a wide range of information received from the ECG leads or from the implanted device and to reprogram the implanted device 10 if needed. The descriptions provided herein with respect to FIG. 3 are intended merely to provide an overview of the operation of programmer 200 and are not intended to describe in detail each and every feature of the hardware and software of the device and is not intended to provide an exhaustive list of the functions performed by the device.

Strain Sensor Embodiments

The general discussion of the stimulation device 10 above has been made with reference to various electrical leads having a substantially conventional configuration and in electrical communication with the stimulation device 10. As discussed above, some of the leads have electrodes that may be used as sensors in order to provide electrical signal feedback or other information to the stimulation device 10 that may in turn use the information to configure a pacing protocol or other treatment parameter. However, in some cases, it may be desirable to use strain sensors instead of or in addition to the electrical sensor capability of the leads that may communicate clinical information to the implantable stimulation device 10 or external programmer 200 in order to better evaluate the type or intensity of therapy needed for the patient. Such strain sensors may be incorporated into a lead body of the leads or may be deployed as a stand alone device in some circumstances.

The use of such strain sensors may be particularly useful for some treatment embodiments that depend on the physical location or movement of tissue, such as physical location and movement data of various portions of the heart including the walls of the right and left atrium, right and left ventricles and septal walls disposed therebetween. To obtain such data, the strain sensors may be deployed as a stand alone device, within a lead body portion of an electrode, or within a body portion of any other suitable medical device, implantable or not, that may include stimulation devices 10, catheters, implantable or temporary, prosthetics such as heart valves and the like. Strain sensor embodiments used for measuring cardiac parameters may be deployed intraluminally, such as within an artery or vein of the heart, epicardially, endocardially or externally by a variety of modalities including transvenous catheterization and non-invasive thoracic access.

Cardiac resynchronization therapy (CRT) is a treatment embodiment that may be enhanced by obtaining such location or physical movement information with respect to heart tissue. CRT is a modality that improves the pumping efficiency of a patient's heart by inducing contemporaneous contraction of both the right and left ventricles. For such a treatment modality, it may be useful to have one or more strain sensors disposed on walls of both the right and left ventricle walls, either endocardially or epicardially. In this way, the physical movement of both ventricles may be monitored in order to evaluate the efficacy of a pacing protocol being used. Strain sensors disposed on or in the septum between the ventricles may also be useful for providing such information. Strain sensors for this type of indication, as well as others, may be small in size in order to be deployable to the desired sites without interfering with cardiac function or such that they may be incorporated into other medical devices. The strain sensors should have a high sensitivity and provide a strong output signal with low noise in order to obtain accurate information. In addition, embodiments of strain sensors that are used for cardiac indications, or other indications where cyclic loading is present, must be durable enough to withstand the cyclic loading over a large number of cycles if the device is to be implanted for any significant length of time.

FIGS. 4-9 illustrate an embodiment of a piezoelectric strain sensor 300 that may be used for the indications discussed above as well as others. The strain sensor embodiment 300 has an elongate rectangular body that is thin relative to the width and length which provides a preferred bending axis or mode. The strain sensor 300 is configured generally as a sandwich type structure with two or more shear layers and one or more piezoelectric elements disposed between the shear layers. Flexible electrical conductors are electrically coupled to the piezoelectric elements in order to communicate an electric voltage signal generated by the piezoelectric elements to an implantable stimulation device 10 or any other suitable device. The entire strain sensor structure is covered with a hermetic seal coating to prevent the ingress of body fluids into the strain sensor structure when the strain sensor is deployed or implanted within a patient's body.

The piezoelectric strain sensor 300 which is configured for use within a patient's body includes a first resilient shear layer 302, a second resilient shear layer 304 disposed apart from and substantially parallel to the first resilient shear layer 302 and a third resilient shear layer 306 disposed apart from and substantially parallel to the second resilient shear layer 304. The third resilient shear layer 306 is also disposed opposite the first resilient shear layer 302 relative to the second resilient shear layer 304. Each resilient shear layer 302, 304 and 306 has a thickness dimension, a minor transverse dimension substantially greater than the thickness dimension and a major transverse dimension that is greater than the minor transverse dimension. For some embodiments, the first resilient shear layer 302, second resilient shear layer 304 and third resilient shear layer 306 have substantially the same shape and size in the transverse dimension and have outer transverse edges which are substantially aligned. For some embodiments, the thickness dimension of the resilient shear layers 302, 304 and 306 may be about 0.001 inch to about 0.04 inch. The minor transverse dimension may be about 0.5 mm to about 5 mm and the major transverse dimension may be about 2 mm to about 20 mm. Also, for some embodiments, the major transverse dimension of the resilient shear layers may be about 1.5 times to about 10 times the minor transverse dimension. The resiliency for the resilient shear layers 302, 304 and 306 may be sufficient to elastically return to an initial relaxed state after a deformation of up to about 10 percent.

The resilient shear layers 302, 304 and 306 may be made from a variety of high strength resilient materials that may be configured to endure extended cyclic loading. Materials such as stainless steel, MP35N, platinum-iridium, titanium and the like may be used for the resilient shear layers 302, 304 and 306 as well as superelastic materials or alloys, such as NiTi alloy and others. These materials may also be coated in whole or part by other materials that enhance the resiliency, radiopacity or other properties. Materials such as platinum, gold or the like may be used to improve the radiopacity of the resilient shear layers 302, 304 and 306 and may be applied by vapor deposition or other suitable processes.

A first piezoelectric element 308 is disposed between the first resilient shear layer 302 and second resilient shear layer 304 transversely away from a longitudinal center line 312 of the first resilient shear layer 302 second resilient shear layer 304. The first piezoelectric element 308 has a first side 314 (FIG. 8) secured to the first resilient shear layer 302 and a second side 316 opposite the first side 314 secured to the second resilient shear layer 304. The piezoelectric element 308 has a thickness dimension between the first side 314 and second side 316, a minor transverse dimension that is substantially greater than the thickness dimension and a major transverse dimension that is greater than the minor transverse dimension and substantially greater than the thickness dimension. The piezoelectric element 308 has a polarization direction extending from the second side 316 to the first side 314 of the piezoelectric element 308 in an orientation that is substantially perpendicular to the second side 316 of the piezoelectric element 308.

A second piezoelectric element 318 (FIG. 6) is disposed opposite the longitudinal center line 312 relative to the first piezoelectric element 308 between the first resilient shear layer 302 and second resilient shear layer 304. The second piezoelectric element 318 has a first side 322 (FIG. 9) secured to the first resilient shear layer 302 and a second side 324 opposite the first side 322 secured to the second resilient shear layer 304. The second piezoelectric element 318 also has a thickness dimension between the first side 322 and second side 324, a minor transverse dimension that is substantially greater than the thickness dimension and a major transverse dimension that is substantially greater than the thickness dimension and greater than the minor transverse dimension. The second piezoelectric element 318 has a polarization direction extending from the first side 322 to the second side 324 of the second piezoelectric element 318 in an orientation that is substantially perpendicular to the first side 322 of the second piezoelectric element 318. The polarization orientation of the second piezoelectric element 318 is substantially parallel to but in the opposite direction of the direction of the polarization orientation of the first piezoelectric element 308.

A third piezoelectric element 326 is disposed transversely away from the longitudinal center line 312 of the second resilient shear layer 304 and third resilient shear layer 306. The third piezoelectric element 326 has a first side 328 secured to the second resilient shear layer 304 and a second side 332 opposite the first side 328 which is secured to the third resilient shear layer 306. The third piezoelectric element 326 also has a thickness dimension between the first side 328 and second side 332, a minor transverse dimension that is substantially greater than the thickness dimension and a major transverse dimension that is greater than that of the minor transverse dimension and substantially greater than the thickness dimension. The third piezoelectric element 326 has a polarization direction extending from the second side 332 to the first side 328 of the third piezoelectric element 326 in an orientation that is substantially perpendicular to the second side 332 of the third piezoelectric element 326 and substantially parallel to the polarization orientation of the first piezoelectric element 308.

A fourth piezoelectric element 334 is disposed opposite the longitudinal center line 312 of the second resilient shear layer 304 relative to the third piezoelectric element 326. The fourth piezoelectric element 334 has a first side 336 secured to the second resilient shear layer 304 and a second side 338, opposite the first side 336, secured to the third resilient shear layer 306. The fourth piezoelectric element 334 also has a thickness dimension between the first side 336 and second side 338, a minor transverse dimension that is substantially greater than the thickness dimension and a major transverse dimension that is greater than the minor transverse dimension and substantially greater than the thickness dimension. The fourth piezoelectric element 334 includes a polarization direction extending from the first side 336 to the second side 338 of the fourth piezoelectric element 334 in an orientation that is substantially perpendicular to the first side 336 of the fourth piezoelectric element 334 and substantially aligned or parallel with the polarization orientation of the second piezoelectric element 318. For the embodiment shown, the first piezoelectric element 308 and third piezoelectric element 326 are disposed in a stacked configuration wherein they are substantially aligned with regard to transverse directions. In addition, the second piezoelectric element 318 and fourth piezoelectric element 334 are also stacked and substantially aligned in transverse directions relative to each other.

Some embodiments of the piezoelectric elements 308, 318, 326 and 334 discussed above may have a thickness dimension of about 10 microns to about 1 mm, a minor transverse dimension of about 0.1 mm to about 5 mm, and a major transverse dimension of about 0.5 mm to about 10 mm. The piezoelectric elements 308, 318, 326 and 334 be made from a variety of suitable materials, such as polycrystalline materials, and may be secured to the respective adjacent resilient shear layers by adhesive bonding, welding, soldering, brazing or the like. The piezoelectric elements 308, 318, 326 and 334 may be secured over an entire contact area between the piezoelectric element and the respective resilient shear layer 302, 304 and 306 or a portion thereof. For the embodiment shown, the piezoelectric elements 308, 318, 326 and 334 are mechanically secured to the respective adjacent resilient shear layers 302, 304 and 306, but are also in electrical contact with the resilient shear layers 302, 304 and 306, which are themselves electrically conductive. As such, a first thin flexible electrical conductor 342 which has a distal end 344 in electrical contact with the first resilient shear layer 302, is in turn, in electrical communication with the first side 314 of the first piezoelectric element 308. A second thin flexible electrical conductor 346 which has a distal end 348 in electrical contact with the third resilient shear layer 306, which is in turn, in electrical communication with the second side 332 of the third piezoelectric element 326. With this arrangement, the first piezoelectric element 308 and third piezoelectric element 326 form a series circuit whereby their output voltages are added together and carried by the first and second electrical conductors 342 and 346. The first and second electrical conductors 342 and 346 also carry the added output voltage signal of the second and fourth piezoelectric elements 318 and 334, as will be discussed in more detail below with respect to FIG. 9.

A compliant filler material 352 (FIG. 7) is disposed between the first resilient shear layer 302 and second resilient shear layer 304. The compliant filler material 352 is also disposed between the second resilient shear layer 304 and third resilient shear layer 306. For the embodiment shown, the compliant filler material 352 completely fills the space between the resilient shear layers 302, 304 and 306 around the piezoelectric elements 308, 318, 326 and 334, however, some embodiments may have less of the space between the resilient shear layers 302, 304 and 306 filled with the compliant material 352. The compliant filler material 352 serves to maintain the physical and electrical separation of adjacent resilient shear layers 302, 304 and 306 while still allowing bending of those layers. Suitable materials 352 may be insulative materials, such as epoxies, heat cured polymers, or any other suitable electrically insulative material with sufficient flexibility. The flexibility of the compliant filler material 352 may vary depending on the stiffness of the resilient shear layers 302, 304 and 306, thickness of the compliant fill material layer 352 and size of the piezoelectric elements 308, 318, 326 and 334, as well as other factors. Some embodiments include a compliant fill material 352 having a shore hardness durometer of about 10 A to about 90 A. The compliant filler material 352 may be bonded to the resilient shear layers 302, 304 and 306 that bound it, or it may float freely between the layers 302, 304 and 306. The composite sandwiched structure of the resilient shear layers 302, 304 and 306, piezoelectric elements 308, 318, 326 and 334 and compliant filler material 352 is configured such that upon bending of the resilient shear layers 302, 304 and 306 due to external forces applied to the resilient shear layers 302, 304 and 306, a shear force is applied on the piezoelectric elements 308, 318, 326 and 334. Some embodiments of the strain sensor 300 are configured such that a $d_{51}$ piezoelectric coefficient is activated in the piezoelectric elements 308, 318, 326 and 334 by shear force applied by the resilient shear layers 302, 304 and 306 onto adjacent piezoelectric elements 308, 318, 326 and 334.

Figure 7:
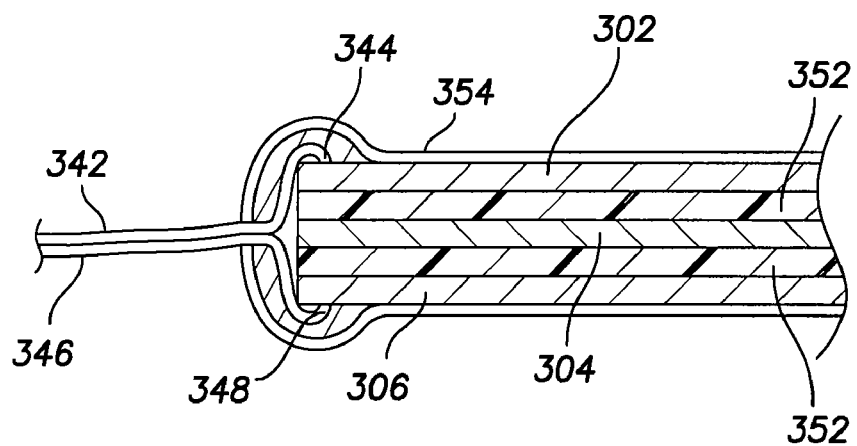
FIG. 7 is an enlarged view indicated by the encircled portion 7-7 of FIG. 6.
Figure 8:
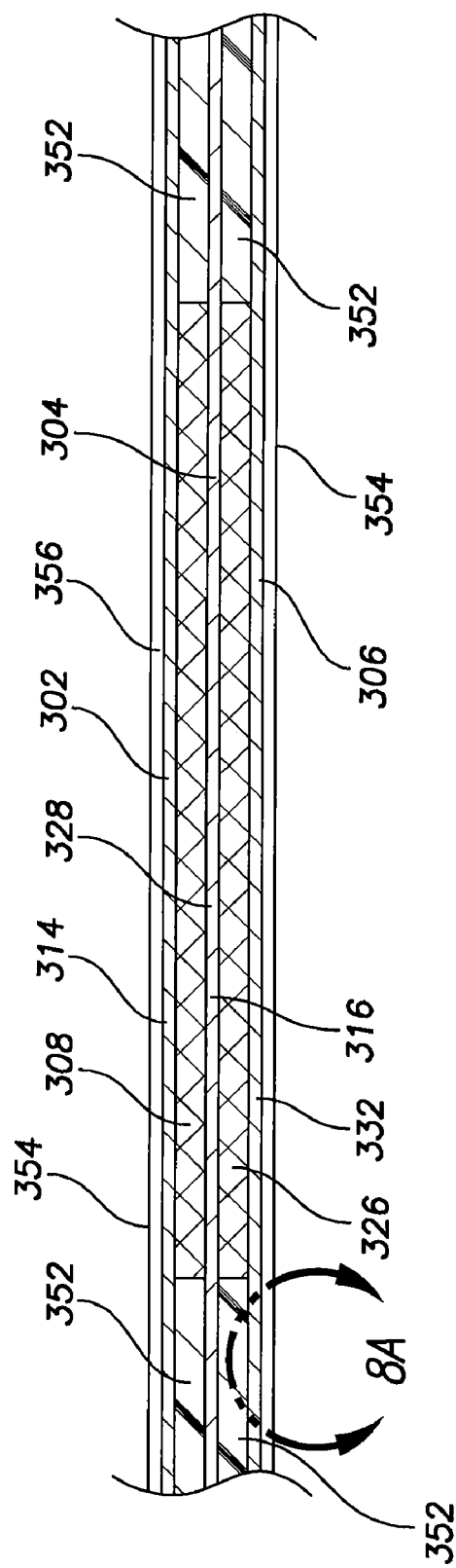
FIG. 8 is an enlarged view indicated by the encircled portion 8-8 of FIG. 6.
Figure 8A:
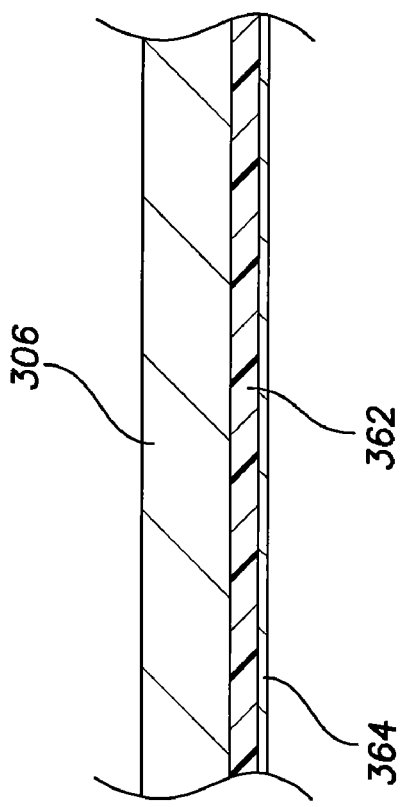
FIG. 8A is an enlarged view indicated by the encircled portion 8A-8A of FIG. 8.

In addition to the compliant fill material 352 disposed between the resilient shear layers 302, 304 and 306, a hermetic seal coating 354 (FIG. 7) may be disposed over external exposed portions of the strain sensor 300 in order to seal the structure of the strain sensor 300 from the ingress of body fluids as well as other contaminants that may affect the performance of the strain sensor 300. As shown in FIGS. 7 and 8, the hermetic seal 354 coating is disposed over an outer surface 356 of the first resilient shear layer 302, an outer surface 358 of the third resilient shear layer 306 and the outer edges of all three resilient shear layers 302, 304 and 306 and the compliant fill material 352. For some embodiments, the hermetic seal coating 354 includes a layer of dielectric material 362 and a metallic layer 364 disposed outside the dielectric layer 362. The layer of dielectric material 362 may include a conformal pin-hole free parylene coating and the metallic layer 364 may include a layer of a thin layer of noble metal, such as platinum or titanium. For some embodiments, the metallic layer 364 may have a thickness of about 0.5 micron to about 2 microns.

Figure 9:
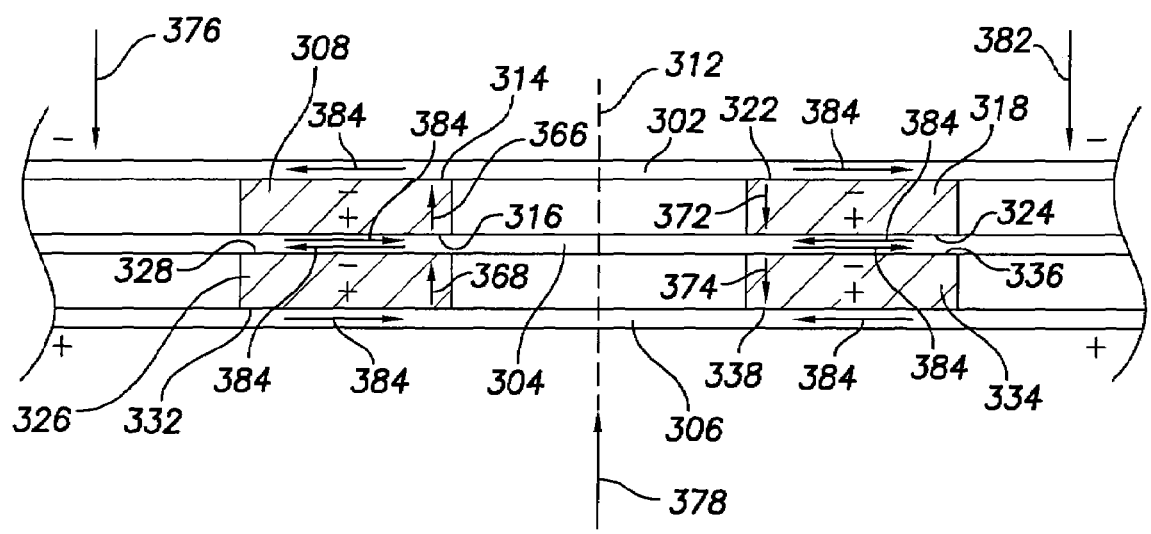
FIG. 9 is a diagrammatic view in longitudinal section of an embodiment of a piezoelectric strain sensor.

FIG. 9 is a diagrammatic view of the strain sensor 300 of FIGS. 4-8 that illustrates the application of bending force on the strain sensor 300 and various resulting shear vectors and electric voltage outputs that result from the application of the bending forces. The output voltages for a particular bending stress will depend on the polarization orientation of each piezoelectric element 308, 318, 326 and 334. As shown, the first, second, third and fourth piezoelectric elements, 308, 318, 326 and 334, are disposed between respective adjacent resilient shear layers 302, 304 and 306. The compliant fill material 352 is not shown for clarity of illustration. The first and third piezoelectric elements 308 and 326 are disposed in a stacked configuration spaced transversely or laterally from the longitudinal center line 312 of the first, second and third resilient shear layers 302, 304 and 306. The first piezoelectric element 308 has a polarization orientation indicated by arrow 366 that extends from the second surface or side 316 of the first piezoelectric element 308 to the first surface or side 314 substantially perpendicular to the second surface 316. The third piezoelectric element 326 has a polarization orientation indicated by arrow 368 that extends from the second surface or side 332 of the third piezoelectric element 326 to the first surface or side 328 substantially perpendicular to the second surface 332. As shown, the polarization orientations of the first and third piezoelectric elements 308 and 326 are substantially aligned with or parallel to each other. As such, if a similar strain configuration is applied to both the first and third piezoelectric elements 308 and 326, they will produce a similarly oriented output voltage signal.

The second and fourth piezoelectric elements 318 and 334 are disposed opposite the first and third piezoelectric elements 308 and 326 relative to the longitudinal center line 312, and are also disposed in a stacked configuration. The second piezoelectric element 318 has a polarization orientation indicated by arrow 372 that extends from the first surface or side 322 of the second piezoelectric element 318 to the second surface or side 324 substantially perpendicular to the first surface 322. The fourth piezoelectric element 334 has a polarization orientation indicated by arrow 374 that extends from the first surface 336 of the fourth piezoelectric element 334 to the second surface 338 substantially perpendicular to the first surface 336. The polarization orientations of the second and fourth piezoelectric elements 318 and 334 are substantially aligned with or parallel to each other. Again, if a similar strain configuration is applied to both the second and fourth piezoelectric elements 318 and 334, they will produce a similarly oriented output voltage signal.

Shear forces on the respective piezoelectric elements 308, 318, 326 and 334 result when a bending force, such as indicated by arrows 376, 378 and 382, is applied to the shear layers 302, 304 and 306 of the strain sensor 300. A bending force wherein arrow 378 represents an upward force directed perpendicular to the plane of the resilient shear layers 302, 304 and 306 at or about the longitudinal center line 312 and balancing downward forces applied to longitudinal edges of the strain sensor 300 indicated by arrow 376 and arrow 382, produces shear strains in the respective piezoelectric elements 308, 318, 326 and 334 as indicated by arrows 384. For such a bending force, the first piezoelectric element 308 is strained such that the first surface 314 is forced away from the longitudinal center line 312 and the second surface 316 is forced towards the longitudinal center line 312. For some embodiments, this shear force configuration will generate a $d_{51}$ coefficient output resulting in an output voltage indicated by the positive and minus signs shown on the first piezoelectric element 308 in FIG. 9. A $d_{51}$ coefficient may be used to produce a high output signal from a given piezoelectric element 308, 318, 326 and 334 relative to other output coefficients for the same piezoelectric element.

The bending force has a similar affect on the third piezoelectric element 326 which produces a similar output voltage signal which is then added to the output voltage signal of the first piezoelectric element 308 which is in turn, communicated to the first and third resilient shear layers 302 and 306. This same bending force produces a similar set of shear strains in the second and fourth piezoelectric elements 318 and 334, but in an opposite direction wherein the second piezoelectric element 318 is strained such that the first surface 322 is forced away from the longitudinal center line 312 in a direction opposite to that of the first surface 314 of the first piezoelectric element 308. The second surface 324 of the second piezoelectric element 318 is forced towards the longitudinal center line 312 in a direction opposite to that of the second surface 316 of the first piezoelectric element 308.

As such, the shear forces on the second and fourth piezoelectric elements 318 and 334 are similar in magnitude and character to those applied to the first and third piezoelectric elements 308 and 326, but in an opposite direction. However, the polarization orientation of the second and fourth piezoelectric elements 318 and 334 is also opposite to that of the first and third piezoelectric elements 308 and 326. The net result of which is that the bending force indicated by arrows 376, 378 and 382 will produce a voltage output signal from the second and fourth piezoelectric elements 318 and 334 that has the same polarity and a similar or same magnitude as the voltage output signal from the first and third piezoelectric elements 308 and 326. The output voltage signals of both stacks of piezoelectric elements 308, 318, 326 and 334 are then communicated to the first and third shear layers 302 and 306, as indicated by the plus sign and minus sign shown next to the respective shear layers in FIG. 9, and ultimately to the first and second electrical conductors 342 and 346. This strain sensor configuration, which produces predominantly shear strains in the piezoelectric elements 308, 318, 326 and 334 of the strain sensor 300, generates a strong output signal relative to the amount of bending force applied to the strain sensor 300.

Figure 10:
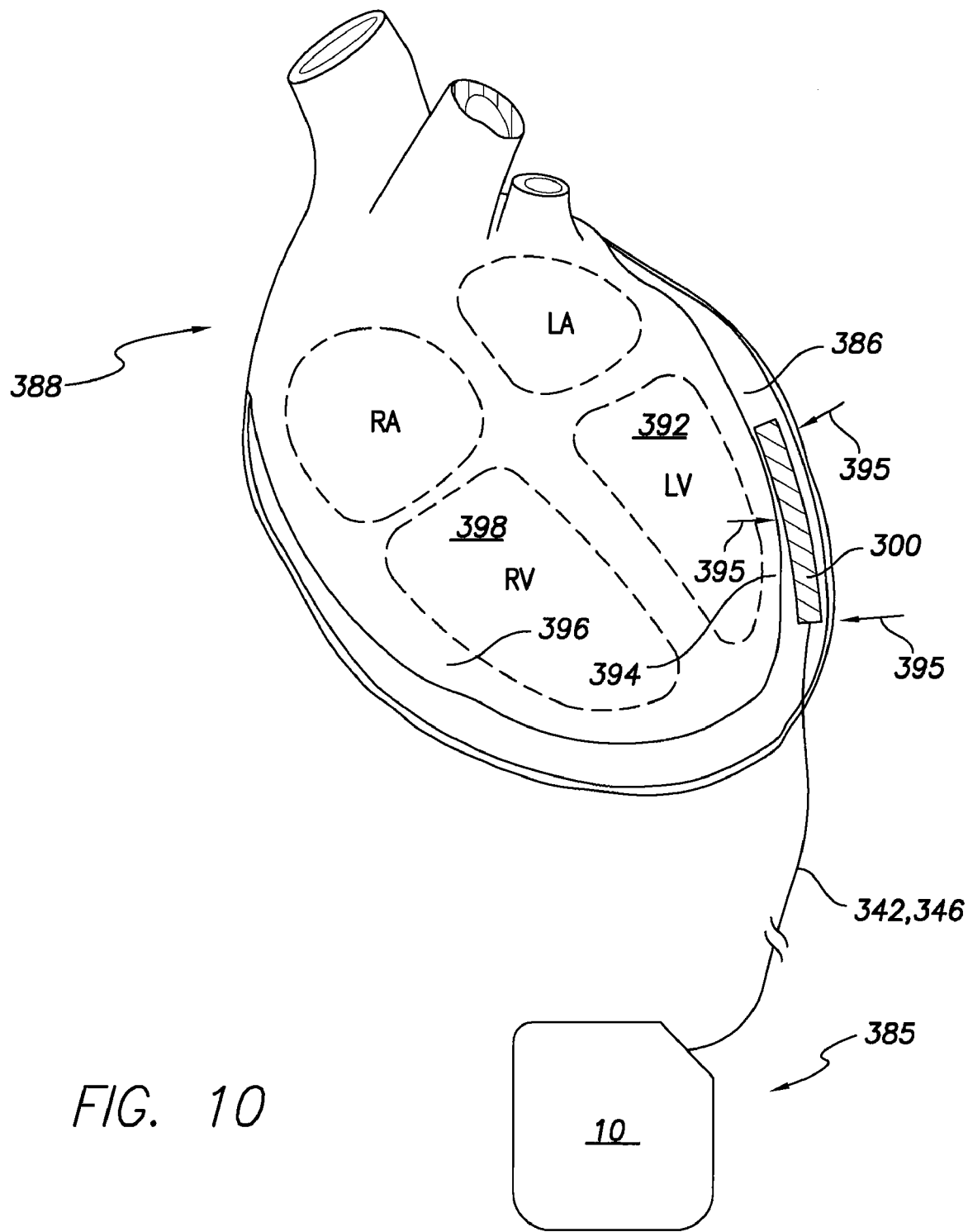
FIG. 10 is a sectional view of an embodiment of a strain sensor disposed in the pericardial space of a patient's heart.

FIG. 10 shows a tissue stimulation system 385 including an implantable stimulation device 10 in communication with the strain sensor embodiment 300. The strain sensor 300 communicates electrically with the implantable stimulation device 10 through the first and second thin flexible electrical conductors 342 and 346, however, other types of communication could be used such as optical signals delivered through optical fibers and the like. The strain sensor 300 is disposed in the pericardial space 386 of the heart 388 adjacent the left ventricle 392. In such a position, the strain sensor 300 may be used to monitor the physical movement of the wall 394 of the left ventricle 392 which may in turn be useful for determining the timing of various therapies, such as stimulation therapies delivered to the heart 388. Bending stress as a result of physical movement of the wall 394 of the left ventricle 392 may produce bending stresses on the strain sensor 300 as indicated by arrows 395, for example. For some embodiments such bending stresses may produce resulting shear stresses in the piezoelectric elements 308, 318, 326 and 334 as shown above with regard to FIG. 9 and the discussion thereof.

If another strain sensor 300 were to be placed adjacent a wall 396 of the right ventricle 398, the physical contraction timing between the two ventricles 392 and 398 may be determined in order to facilitate the delivery of CRT for treatment of congestive heart failure or other conditions that affect the efficiency of the heart 388. Epicardial access may be achieved by any suitable method for such placement of the sensor into the pericardial space 386, such as a non-invasive subxiphoid technique. In addition to the subxiphoid deployment method discussed above, it may also be desirable to deploy some or all of the strain sensor embodiments discussed herein by a transvenous approach. For example, U.S. Pat. No. 4,998,975, by Cohen et al., describes useful transvenous deployment methods and is incorporated by reference herein in its entirety.

Figures 11, 12:
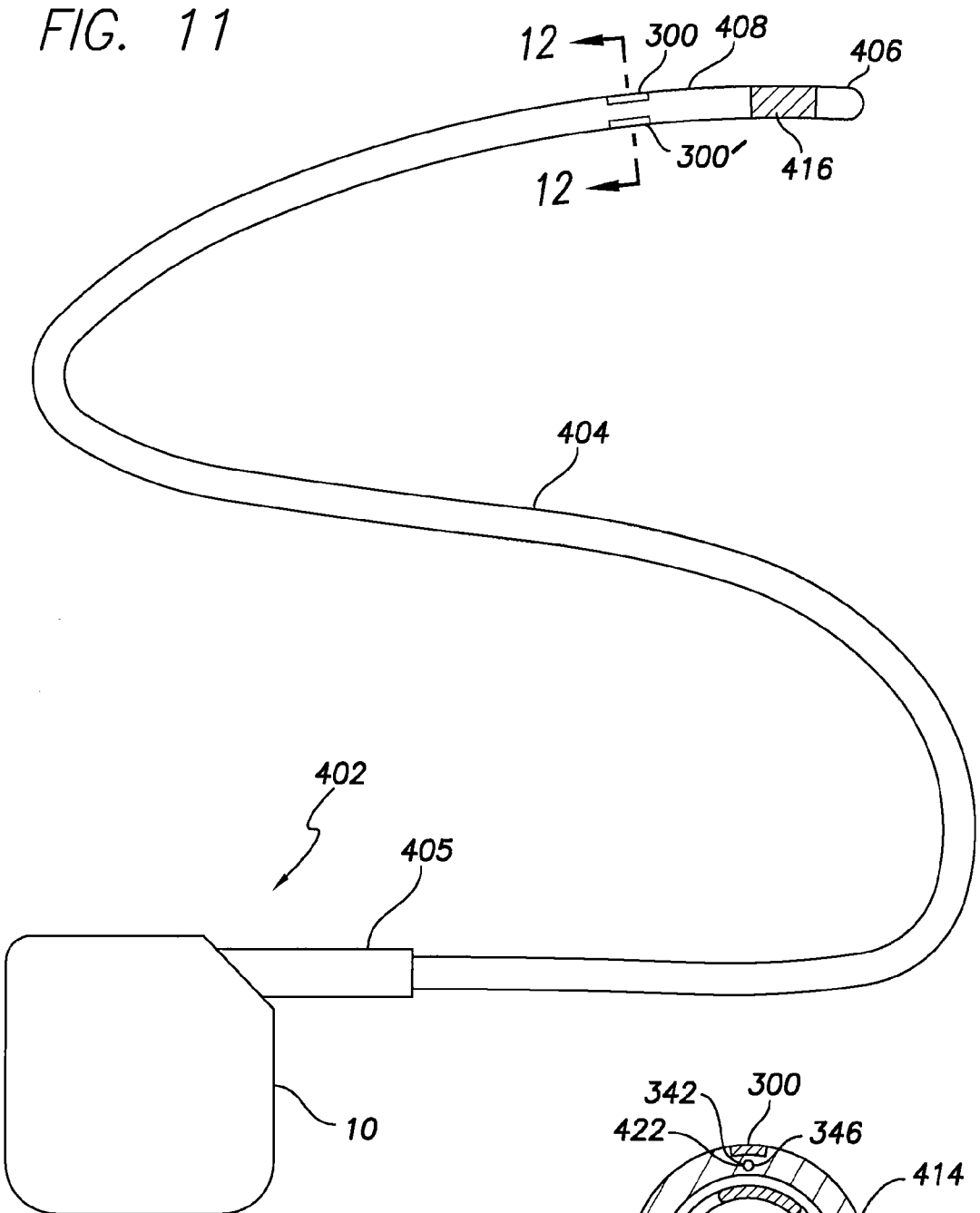
FIG. 11 is an elevational view of an embodiment of a lead having a strain sensor disposed on a distal portion thereof.
FIG. 12 is an enlarged view in transverse cross section of the lead of FIG. 11 taken along lines 12-12 of FIG. 11.

FIGS. 11 and 12 illustrate another embodiment of a tissue stimulation system 402 having an implantable electrical lead 404, with a proximal connector 405 and a proximal conductive terminal (not shown) which is electrically coupled to the implantable stimulation device 10. The lead 404 also has a distal end 406, a distal section 408, an inner lumen 412 and a coiled conductor 414 extending within the inner lumen 412. A ring electrode 416 is electrically coupled to the coiled conductor 414 and is disposed on the distal section 408. Such a ring electrode 416 may be used for delivery of pacing signals, or the like, to a patient's heart 388. A first strain sensor 300 and second strain sensor 300' are also disposed on opposite sides of the distal section 408 of the lead 404 in a wall or body portion 418 of the lead 404. The strain sensors 300 and 300' are in communication with the stimulation device 10 via electrical conductors 342 and 346 that extend proximally from the respective strain sensors 300 and 300' within a first conductor lumen 422 and second conductor lumen 424 formed into the lead body 418.

Figure 13:
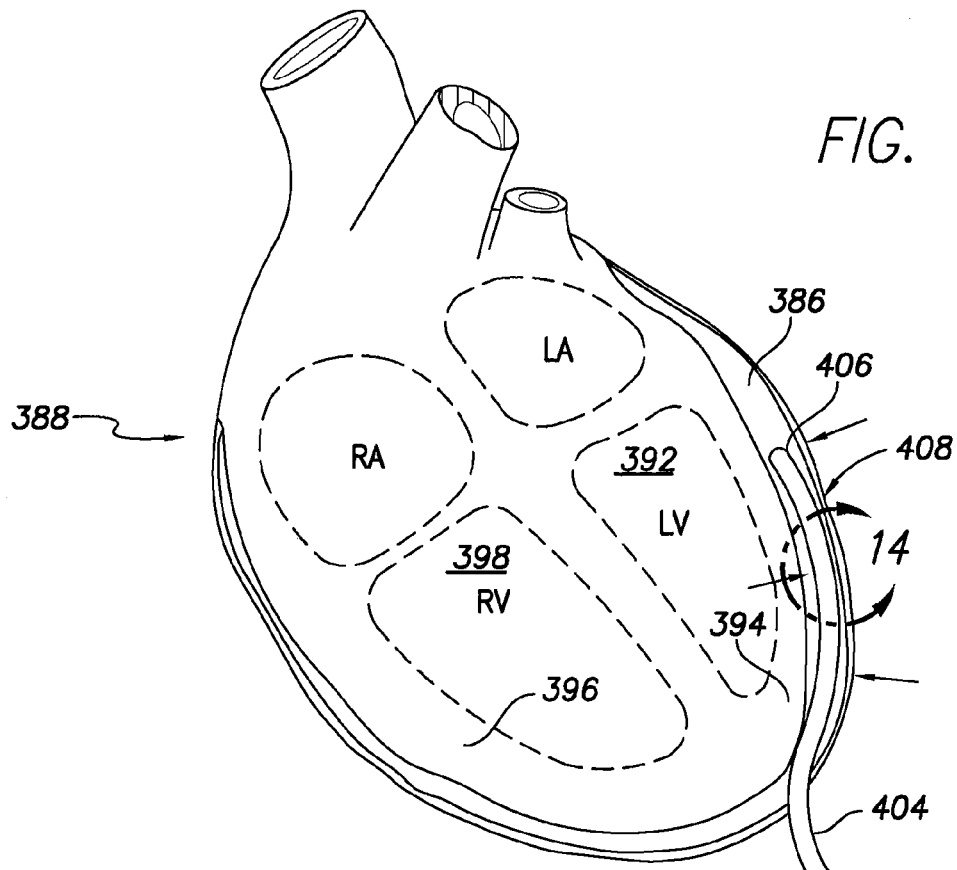
FIG. 13 is a sectional view of the strain sensor of the lead of FIG. 11 disposed within the pericardial space of a patient's heart.
Figure 14:
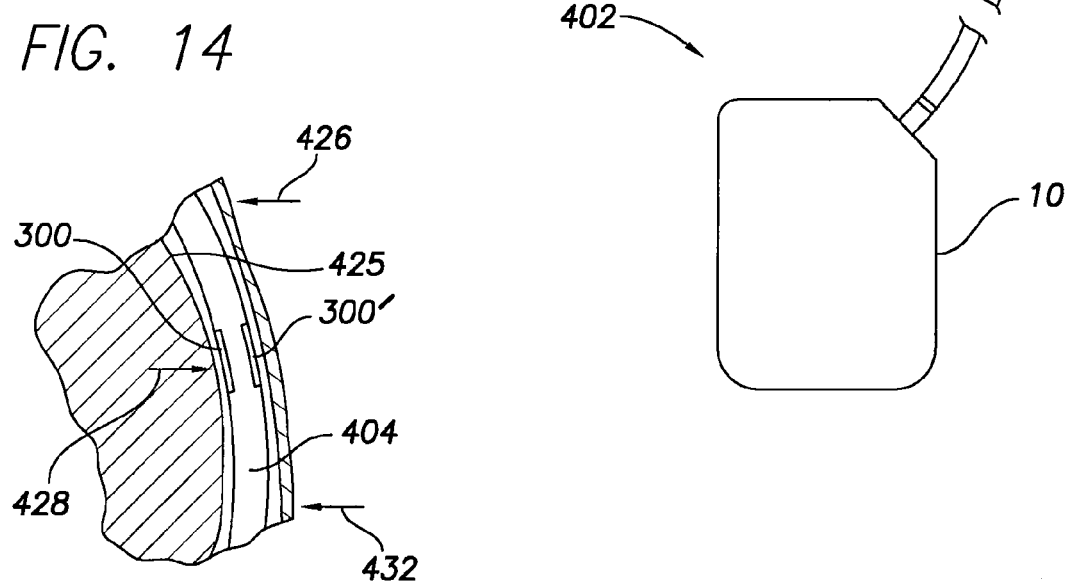
FIG. 14 is an enlarged sectional view indicated by the encircled portion 14-14 of FIG. 13.

FIGS. 13 and 14 show the distal section 408 of the lead 404 of the tissue stimulation system 402 of FIGS. 11 and 12 disposed within the pericardial space 386 of a patient's heart 388. FIG. 14 shows the first strain sensor 300 disposed against epicardial tissue 425 of the patient's heart 388 and subject to bending forces as a result of movement of the epicardial tissue 425. As an example, FIG. 14 shows bending forces indicated by arrows 426, 428 and 432, which may be generated by relaxation, or some other type of physical movement, of the wall 394 of the left ventricle 392. This type of bending force may then produce bending strains and resulting shear strains on the piezoelectric elements 308, 318, 326 and 334 of the strain sensors 300 or 300', depending on the respective orientation of the strain sensors, which are similar to or the same as the shear strains illustrated in FIG. 9. Such shear strains may produce a similar output voltage signal to that of FIG. 9 as well.

In general, a wide variety of techniques can be implemented consistent with the principles the invention and no attempt is made herein to describe all possible techniques. Although described primarily with reference to embodiments wherein the implanted stimulation device is a defibrillation/pacer, the principles discussed herein are applicable to other implantable medical devices as well. The various functional components of the exemplary embodiments may be implemented using any appropriate technology including, for example, microprocessors running software programs or application specific integrated circuits (ASICs) executing hard-wired logic operations. With regard to the above detailed description, like reference numerals used therein refer to like elements that may have the same or similar dimensions, materials and configurations. While particular forms of embodiments have been illustrated and described, various modifications can be made without departing from the spirit and scope of the embodiments of the invention. Accordingly, it is not intended that the invention be limited by the forgoing detailed description.

What is claimed is:

1. A piezoelectric strain sensor for use within a patient's body, comprising:
   a first resilient shear layer;
   a second resilient shear layer disposed apart from and substantially parallel to the first resilient shear layer;
   a piezoelectric element disposed between the first resilient shear layer and the second resilient shear layer with the first resilient shear layer and second resilient shear layer configured to apply shear strain onto the piezoelectric element upon bending of the first resilient shear layer and second resilient shear layer; and
   a compliant filler material disposed between the first resilient shear layer and second resilient shear layer.

2. The strain sensor of claim 1 further comprising a hermetic seal coating disposed over external exposed portions of the strain sensor.

3. The strain sensor of claim 2 wherein the hermetic seal coating comprises a layer of dielectric material and a metallic layer outside the dielectric material.

4. The strain sensor of claim 3 wherein the dielectric material comprises a conformal pin-hole free parylene coating.

5. The strain sensor of claim 3 wherein the metallic layer comprises a thin layer of noble metal.

6. The strain sensor of claim 1 wherein the piezoelectric element comprises a first side secured to the first resilient shear layer, a second side opposite the first side and secured to the second resilient shear layer, a thickness dimension between the first side and the second side, a major transverse dimension that is substantially greater than the thickness dimension and a polarization direction extending from the second side to the first side of the piezoelectric element in an orientation that is substantially perpendicular to the second side of the piezoelectric element.

7. The strain sensor of claim 6, wherein the piezoelectric element is configured such that a $d_{51}$ piezoelectric coefficient is activated in the piezoelectric element by shear force applied by the first resilient shear layer and second resilient shear layer.

8. The strain sensor of claim 1 further comprising a second piezoelectric element disposed between and secured to the first resilient shear layer and second resilient shear layer with the first resilient shear layer and second resilient shear layer configured to apply shear strain onto the second piezoelectric element upon bending of the first resilient shear layer and second resilient shear layer.

9. The strain sensor of claim 8 wherein the compliant filler material is disposed between the first resilient shear layer and second resilient shear layer around the first and second piezoelectric elements.

10. The strain sensor of claim 8 wherein the piezoelectric elements are disposed on opposite sides of a longitudinal center line of the first resilient shear layer and a longitudinal center line of the second resilient shear layer.

11. The strain sensor of claim 1 wherein at least one of the first resilient shear layer and the second resilient shear layer comprises a superelastic material.

12. The strain sensor of claim 11 wherein the superelastic material comprises NiTi alloy.

13. The strain sensor of claim 1 wherein the piezoelectric element is disposed laterally away from a longitudinal center line of the first resilient shear layer and a longitudinal center line of the second resilient shear layer.

14. The strain sensor of claim 1 wherein the first resilient shear layer and second resilient shear layer have substantially the same shape and size in the transverse dimensions and have outer edges which are aligned.

15. A piezoelectric strain sensor for use within a patient's body, comprising:
a first resilient shear layer;
a second resilient shear layer disposed apart from and substantially parallel to the first resilient shear layer;
a first piezoelectric element disposed transversely away from a longitudinal center line of the first resilient shear layer and a longitudinal center line of the second resilient shear layer and having a first side secured to the first resilient shear layer, a second side opposite the first side and secured to the second resilient shear layer, a thickness dimension between the first side and the second side, a major transverse dimension that is substantially greater than the thickness dimension, a polarization direction extending from the second side to the first side of the first piezoelectric element in an orientation that is substantially perpendicular to the second side of the first piezoelectric element;
a second piezoelectric element disposed transversely on an opposite side of the longitudinal center line of the first resilient shear layer from the first piezoelectric element and having a first side secured to the first resilient shear layer, a second side opposite the first side and secured to the second resilient shear layer, a thickness dimension between the first side and the second side, a major transverse dimension that is substantially greater than the thickness dimension, a polarization direction extending from the first side to the second side of the second piezoelectric element in an orientation that is substantially perpendicular to the first side of the second piezoelectric element; and
a compliant filler material disposed between the first resilient shear layer and second resilient shear layer.

16. The strain sensor of claim 15 further comprising:
a third resilient shear layer disposed apart from and substantially parallel to the second resilient shear layer;
a third piezoelectric element disposed transversely away from a longitudinal center line of the second resilient shear layer and a longitudinal center line of the third resilient shear layer and having a first side secured to the second resilient shear layer, a second side opposite the first side and secured to the third resilient shear layer, a thickness dimension between the first side and the second side, a major transverse dimension that is substantially greater than the thickness dimension, a polarization direction extending from the second side to the first side of the third piezoelectric element in an orientation that is substantially perpendicular to the second side of the third piezoelectric element;
a fourth piezoelectric element disposed transversely on an opposite side of the longitudinal center line of the second resilient shear layer from the third piezoelectric element and having a first side secured to the second resilient shear layer, a second side opposite the first side and secured to the third resilient shear layer, a thickness dimension between the first side and the second side, a major transverse dimension that is substantially greater than the thickness dimension, a polarization direction extending from the first side to the second side of the fourth piezoelectric element in an orientation that is substantially perpendicular to the first side of the fourth piezoelectric element; and
a compliant filler material disposed between the first resilient shear layer and second resilient shear layer.

17. The strain sensor claim 16 wherein the first piezoelectric element and third piezoelectric element are substantially aligned in transverse directions in a stacked configuration.

18. The strain sensor of claim 17 wherein the second piezoelectric element and fourth piezoelectric element are substantially aligned in transverse directions in a stacked configuration.

19. The strain sensor of claim 15 wherein the piezoelectric elements are configured such that a $d_{51}$ piezoelectric coefficient is activated in the piezoelectric elements by shear force applied by the respective resilient shear layers.

20. The strain sensor of claim 15 further comprising a first electrical conductor in electrical communication with the first side of the piezoelectric elements and a second electrical conductor in electrical communication with the second side of the piezoelectric elements.

21. An implantable piezoelectric strain sensor comprising a hermetic seal coating having a dielectric layer and a thin noble metal layer disposed outside of the dielectric layer.

22. The strain sensor of claim 21 wherein the dielectric material comprises a conformal pin-hole free parylene coating.

23. The strain sensor of claim 21 wherein the thin metallic layer has a thickness of about 0.5 micron to about 2 microns.

24. The strain sensor of claim 21 wherein the a material of the thin metallic layer is selected from platinum or titanium.

25. A tissue stimulation system comprising:
an implantable stimulation device; and
a strain sensor in communication with the implantable stimulation device, the strain sensor including:
a first resilient shear layer;

a second resilient shear layer disposed apart from and substantially parallel to the first resilient shear layer;

a piezoelectric element disposed between the first resilient shear layer and the second resilient shear layer with the first resilient shear layer and second resilient shear layer configured to apply shear strain onto the piezoelectric element upon bending of the first resilient shear layer and second resilient shear layer; and a compliant filler material disposed between the first resilient shear layer and second resilient shear layer.

26. The system of claim 25 wherein the strain sensor is in electrical communication with the implantable stimulation device.

27. The system of claim 25 further comprising a lead in electrical communication with the implantable stimulation device, wherein the strain sensor is disposed within or on a body portion of the lead.

* * * * *